(12) United States Patent
Yoshida et al.

(10) Patent No.: US 6,740,328 B2
(45) Date of Patent: May 25, 2004

(54) SOLID COSMETICS

(75) Inventors: Kunihiko Yoshida, Yokohama (JP); Tomiyuki Nanba, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 95 days.

(21) Appl. No.: 10/097,579

(22) Filed: Mar. 15, 2002

(65) Prior Publication Data

US 2003/0012754 A1 Jan. 16, 2003

(30) Foreign Application Priority Data

Mar. 21, 2001 (JP) ........................................ 2001-080574

(51) Int. Cl.⁷ ............................ A61K 7/00; A61K 7/025
(52) U.S. Cl. ................................. 424/401; 424/64
(58) Field of Search ............................. 424/64, 401, 63

(56) References Cited

U.S. PATENT DOCUMENTS 5,948,394 A * 9/1999 Walling et al. ................ 424/64

FOREIGN PATENT DOCUMENTS

| JP | 07-149613 | 6/1995 |
|---|---|---|
| JP | 07-196437 | 8/1995 |
| JP | 08-059428 | 3/1996 |
| JP | 10-017432 | 1/1998 |

* cited by examiner

Primary Examiner—James M. Spear
Assistant Examiner—Sharon Howard
(74) Attorney, Agent, or Firm—Snider & Associates; Ronald R. Snider

(57) ABSTRACT

A solid cosmetic composition, which drastically improves the shape-retaining ability and usability, which has a good, tender feeling, good spreadability when applied and is glossy looking is provided by use of a wax composition solidifier, which has a good shape-retaining ability without use of a conventional solidifier such as ceresin is provided. A solid cosmetic composition has (a) Fischer-Tropsch wax having average molecular weight of 300 to 1200 and (b) Microcrystalline wax in the weight ratio of (a):(b)=60:40 to 99.9:0.1

8 Claims, No Drawings

SOLID COSMETICS

RELATED APPLICATIONS

This application claims the priority of Japanese Patent Application No, 2001-80574 filed on Mar. 21, 2001, which is incorporated herein by reference.

BACKGROUND OF THE INVENTION

1. Field of the Invention

The present invention relates to a solid cosmetic composition. More particularly, the present invention relates to a solid cosmetic composition with superior shape-retaining ability, superior spreadability, and gloss.

2. Description of the Related Art

In the cosmetic field, lipstick, lip-balm, foundation, pencil shaped cosmetics, and hair stick are known as solid cosmetic compositions.

Among these, oil-based solid cosmetic compositions is (a) a liquid oil component such as caster oil, jojoba oil, squalene, lanolin, chemically synthesized ester oil, liquid paraffin, and (b) a wax component which is a solidifier such as carnauba wax, candelilla wax, ceresin wax, microcrystalline wax, hydrogenated animal oil, hydrogenated vegetable oil, beeswax, and (c) a powder component. The powder component is dispersed in the mixture of liquid oil component and wax component.

Generally, the product must satisfy the shape-retaining ability and usability. Usability requires especially good spreadability and gloss, which is controlled by the blending ratio of a wax component and a liquid oil component. But it is quite difficult to satisfy the demands for enough shape-retaining ability and good usability simultaneously. Because the wax component is an essential ingredient for solidifying the liquid oil component, it should be a large amount of the formula in order to retain the product shape while in use and in order to allow storing at various temperatures. When the amount of the wax component is high, spreadability of the product tends to be heavy, and the gloss that is provided by the liquid oil component tends to be decreased. Because of this contradiction, it is difficult to satisfy the demands for enough shape-retaining ability and good usability simultaneously. It is also demanded that a solid cosmetic composition have superior shape-retaining ability and usability for a long period of time.

In order to solve the above-mentioned problem, a small amount of wax giving high hardness to the product may be selected Such a wax usually has a high melting point and there is a problem that it is not easy to produce. Such a wax requires additional heating process in order to melt the wax ingredient at a high temperature during production and the filling property tends to become undesirable due to the relatively high melting point. Further more, when the solid cosmetic composition contains water such as an emulsified type lipstick, extra heating at high temperature causes loss of the water ingredient.

BRIEF SUMMARY OF THE INVENTION

An object of the present invention is to provide a solid cosmetic composition, which dramatically improves the shape retaining ability and usability without an extra heating process, which avoids a problem of the high melting point of the wax ingredient.

The inventors conducted research to solve the aforementioned problem and discovered that when combining a) Fischer-Tropsch wax having average molecular weight of 300 to 1200 and b) Microcrystalline wax in a specific ratio, that the liquid oil component when solidified was unexpectedly high hardness. It was without loss of good spreadability and gloss and extra heating process during the production.

The present invention relates to a wax composition, which gives enough hardness to a product such as solid cosmetics, which contain a liquid oil component. The invention provides solid cosmetics having superior shape-retaining ability and spreadability and gloss. The aforementioned problem due to the high melting point of wax ingredient is eliminated.

The present invention relates to a solid cosmetic composition comprising:
- (a) Fischer-Tropsch wax having an average molecular weight of 300 to 1200 and
- (b) Microcrystalline wax and (a):(b)=60:40 to 99.9:0.1 by weight ratio.

The present invention relates to a solid cosmetic composition further comprising a liquid oil component.

The present invention relates to a solid cosmetic composition comprising a solidifier consisting of wax components (a) and (b).

The present invention relates to a solid cosmetic composition further comprising a colorant and/or pigment.

The present invention relates to a solid cosmetic composition such as lip stick.

The present invention relates to a wax composition comprising:
- (a) Fischer-Tropsch wax having average molecular weight of 300 to 1200.
- (b) Microcrystalline wax and (a):(b)=60:40 to 99.9:0.1 by weight ratio.

BEST MODE FOR CARRYING OUT THE INVENTION

The present invention is described in detail below.

In the present invention, the ingredient (a) Fischer-Tropsch wax is a synthetic hydrocarbon wax, obtained by the "Fischer-Tropsch synthesis", which has an average molecular weight of 300 to 1200, and preferably 400 to 1100, and more preferably 500 to 700.

When the average molecular weight of Fischer-Tropsch wax is less than 300, solidability tends to be decreased. When the average molecular weight of Fischer-Tropsch was is more than 1200, the melting point of the wax is too high to produce the produce the product and extra processes are required. The average molecular weight in this specification is calculated by a conventional method, and it is defined as "Mean average molecular weight," which is the number-average molecular weight.

In the present invention, an average molecular weight in the above mentioned range is necessary. It is preferable to use a Fischer-Tropsch wax having a molecular distribution curve with a sharp peak, in order to close to single distribution of the molecular range.

Fischer-Tropsch wax in the present invention is available as commercial product. For example, commercial products having an average molecular weight of 300 to 1200 are as follows: "Paraflint C77", "ParaflintC80", "Paraflint H1" (Products of SCHUMANN SAZOL.LTD.) "FT100", "MDP-7010" (Products of NIPPON SEIRO CO., LTD.)

The amount of the ingredient (a) is defined according to the aforementioned specific range of the ratio of ingredient (a) and (b), it is preferably 0.06 to 29.97 mass %, more preferably 0.6 to 19.98 mass %, and more preferably 3.0 to 14.98 mass % in the total solid cosmetic composition.

For Ingredient (b) of the present invention, microcrystalline wax is a hydrocarbon wax conventionally used in cosmetic compositions such as lipstick, creams and the like. It uses a commercially available material. It is preferable that the Microcrystalline wax have a melting point which is 70° C. or more, and less than 100° C. and more preferably more than 80 to 95° C. for best shape-retaining ability. The amount of the ingredient (b) Microcrystalline wax formulated in the present invention is 0.01 to 12 mass %, preferably 0.05 to 8 mass %, more preferably 0.25 to 6 mass % in the total solid cosmetic composition.

In the present invention, when the wax composition, the blended ingredients (a) and (b) are in the ratio of (a):(b)= 60:40 to 99.0:0.1 (in mass ratio), the composition can be used as solidifier in a solid cosmetic composition.

The blend ratio of (a) and (b) is preferably (a):(b)=80:20 to 99.8:0.2 (in mass ratio), and more preferably (a):(b)= 90:10 to 95:5 (in mass ratio).

When ingredients (a) and (b) are blended in aforementioned ratio, the hardness of the product has a critical point and the wax component has an excellent effect as solidifier.

In the present invention, the wax component is blended just by mixing ingredient (a) and (b), in the aforementioned ratios, and the pre-mixed wax component can be used for raw material for solid cosmetics. Furthermore, ingredients (a) and (b) can be separately mixed to a liquid oil component and blended into the solid cosmetic composition in the process of the production.

Since this wax composition gives only enough hardness to the solid cosmetic composition, spreadability and gloss are not deteriorated. The solid cosmetic composition containing this wax composition has an excellent shape-retaining ability without a problem of a high melting point in the production process.

The wax composition of the present invention has a good solidifier property for the liquid oil component. It has great value as a substitute material for the conventionally used solidifier such as ceresin wax.

The amount of the wax composition (total amount of ingredient (a) and (b)) to total amount of the solid cosmetic composition, it is defined according to the type of solid cosmetic composition. It is preferably 0.1 to 30 mass % of total amount of a solid cosmetic, more preferably 1 to 20 mass %, more particularly preferably 5 to 15 mass % to total amount of a solid cosmetic. If the blend ratio is less than 0.1 mass %, the solidifier effect is not performed and the shape-retaining ability of the product tends to be a problem On the other hand, if the blend ratio is more than 30 mass %, the hardness of the product of the solid cosmetic tends to be too hard and good spreadability and gloss tend to deteriorate.

In the present invention, the liquid oil component is in a liquid form at ordinary temperatures (15° C.). The oil is not limited and available for this invention if the oil is usable for cosmetics.

Preferably examples of the liquid oil component are as follows:

Glyceryl tri-2-ethylhexsanoate, glyceryl diisostearate, diisostearyl malate, dimethyl polysiloxane, decamethyl pentasiloxane, macademia nuts oil, trimethylolpropane trioctanoate, diglyceryl triisostearate, heptyldecyl hydroxystearate, jojoba oil, squarane, liquid lanolin, glyceryl triisostearate/hydrogenated rosinate, methylphenyl polysiloxane, glyceryl triusostearate, and polybutene.

It is particulaly preferable for lipstick compositions and other compositions for lips, to use liquid lanolin, glyceryl triisostearate/hydrogenated rosinate, methylphenyl polysiloxane, glyceryl triisostearate, or polybutene.

It is preferable in terms of long lastingness (lasting power: staying on the skin for long time against a sebum) when it is applied to the skin, to use volatile liquid oils (ring type silicone oils such as octamethylcyclotetrasiloxane, decamethylcyclopentasiloxane, dodecamethylcyclohexasiloxane).

The amount of liquid oil component formulated in the present invention is preferably 30 to 99.9 mass %, and more preferably 50 to 59 mass % in the total solid cosmetic composition.

When the amount of liquid oil component is little, spreadability tends to be heavy.

In the present invention of a solid cosmetic composition, in addition to a liquid oil, if necessary, it can also be blended into a solid oil component and/or into semi-solid oil component.

In addition to the aforementioned essential ingredients, any other ingredients, which are commonly blended in solid cosmetic compositions, can be blended in if they do not deteriorate the effect of the present invention. For example: other waxes, other oils, humectants, preservatives, antioxidants, ultraviolet absorbers, ultraviolet scattering agents, polymers, surface active agents, colorants, pigments, powders, drugs, alcohols, solvents, fragrances, flavors, etc, are available. The solid cosmetic composition of the present invention can be produced by common production process.

In the present invention, specific examples of solid cosmetic compositions are as follows: Make-up cosmetics such as lipstick, lip-gloss, lip balm, foundations, eye shadow, hair cosmetics such as hair stick, and pomades are examples. The solid cosmetic compositions refer to a broad range of compositions used for cosmetics and are not limited to a solid cosmetic composition. A stick form solid cosmetic is preferable, especially a lipstick containing a pigment and/or a colorant.

In the present invention, the solid cosmetic composition is in solid form at ordinary room temperature (25° C.).

The solid cosmetic composition of the present invention having superior shape-retaining ability and usability is obtained by blending a wax component of aforementioned ingredient (a) having particular average molecular weight, and the ingredient (b). Reason of the effect is not known, but it is believed to be as follows.

The solid cosmetic composition comprising the wax component and the liquid oil component has a network structure of a wax component in micro crystal form, when the wax and oil are combined with each other, the liquid oil component is included in this structure and the shape stays in solid form.

The shape and size of the wax micro-crystal structure, and the types of the liquid oil components form the structure and character of the solid cosmetics. The wax composition of the present invention is balanced to maximize the shape-retaining ability and usability by solidifying the liquid oil component.

EXAMPLES

The present invention is described in detail below based on examples: however, the present invention is not limited to these Examples. The blend ratio is shown as a mass % value of the total amount of the composition unless specified otherwise.

Test of Solidification: Wax Composition

Tests were conducted on wax compositions that were mixed with ingredients (a) and (b) in different blending rates and solidifications of the liquid oils. For Ingredient (a), Fischer-Tropsch wax having average molecular weight 530 (Paraflint C77 product of SCHUMANN SAZOL. LTD) was used.

Test samples (which are usable as lip gloss) were prepared by mixing 10 mass % of Wax composition (in Table 1) and 90 mass % of liquid oil (Glyceryl tri-2-ethylhexanoate). The hardness was measured by a Card tension meter (Type No.M-301AR, Product of IIO Electric Co. Ltd).
Condition: Test samples were left under 37° C. for 1 hour, measured by 800 g load, and 3φ (diameter of a pressure sensitive shaft) at 37° C.

The test results are shown in the following Table 1.

The wax amount in Table 1 is a concentration of the wax in the wax composition.

As it is clearly indicated in Table 1, the hardness of the test sample was increased critically when the blending ratio of (a) and (b) is (a):(b)=60:40 to 99.9:0.1, preferably (a):(b)= 80:20 to 99.8:0.2, and more preferably (a):(b)=90:10 to 95:5.

When the blending ratio is in aforementioned specific range, the wax composition has a remarkable hardness. The aforementioned specific range has critical meaning in the present invention.

It is an unexpected result that the wax composition mixed with ingredients (a) and (b) in the specific ratio solidifies the liquid oil in maximum hardness. It is preferable to use the wax composition of a specific blending ratio for obtaining a maximum hardness. Also, the aforementioned wax composition does not have any problem concerning to the melting point during the process of production for a solid cosmetic.

Shape-retaining Ability
Shape-retaining ability was evaluated based on the inspection after filling and molding.
Evaluation
◎: Fairly good (Solidified in fairly good condition)
○: Good (Solidified in good condition)
Δ: Not good (Solidified but too soft and in paste condition)
X: Bad (Not solidified and in liquid condition)
Spreadability
Each member of a panel of 20 specialists conducted the following five step evaluation, based on which the spreadability was evaluated.
Score
5: Spreadability is good (light)
4: Spreadability is somewhat good (somewhat light)
3: Spreadability is normal
2: Spreadability is somewhat bad (somewhat heavy)
1: Spreadability is bad (heavy)
Evaluation
◎: The average score is 4.0 or more and 5.0 or less
○: The average score is 3.0 or more and less than 4.0
Δ: The average score is 2.0 or more and less than 3.0
X: The average score is 1.0 or more and less than 2.0
Gloss
Each member of a panel of 20 specialists conducted the following five step evaluation, based on which the gloss was evaluated.

TABLE 1

| Sample | a | b | c | d | e | f | g | h | i | j | k | l |
|---|---|---|---|---|---|---|---|---|---|---|---|---|
| Fischer-Tropsch wax | 100 | 99.9 | 99.8 | 95 | 90 | 85 | 70 | 60 | 50 | 40 | 20 | 0 |
| Microcrystalline wax | 0 | 0.1 | 0.2 | 5 | 10 | 15 | 30 | 40 | 50 | 60 | 80 | 100 |
| Hardness of the solid sample | 11 | 14.3 | 17.8 | 21.8 | 20.5 | 18.8 | 13.8 | 12 | 10.3 | 9.5 | 8.5 | 8 |

Test of a Solid Cosmetic Composition

The solid cosmetic compositions were produced according to the following tables, and the effect of the present invention was evaluated.
The Preparation Method of the Solid Cosmetics of Table 2–Table 9:

The ingredients were dissolved at 120° C. and dispersed with a disper. Following deaeration, the mixture was poured into container or give and cooled to obtain a solid cosmetic.
The Preparation Method of the Lip Rouge Composition of Table 10:

The ingredients (1)–(7), (10)–(16) were dissolved at 90 to 1000° C. and dispersed with a disper. Ingredients (8) and (9) were added to the aforementioned mixture, following deaeration. The mixture was poured into a lipstick container and cooled to obtain a stick-shaped emulsified lipstick composition. The Fischer-Tropsch waxes that are used in Table 2 to Table 10 were as follows: Fisher-Tropsch wax (1)=Paraflint C77 (mean average molecular weight, which is the number-average molecular weight, is 530) Fisher-Tropsch wax (2)=Paraflint C80 (mean average molecular weight, which is the number-average molecular weight, is 630) Fisher-Tropsch wax (3)=Paraflint Hi (mean average molecular weight, which is the number-average molecular weight, is 1060)
Evaluation Criteria In the Examples, the samples were evaluated with the following criteria for shape-retaining ability, spreadability, and gloss.

Score
5: Gloss is good
4: Gloss is somewhat good
3: Gloss is normal
2: Gloss is somewhat poor
1: Gloss is poor
Evaluation
◎: The average score is 4.0 or more and 5.0 or less
○: The average score is 3.0 or more and less than 4.0
Δ: The average score is 2.0 or more and less than 3.0
X: The average score is 1.0 or more and less than 2.0

TABLE 2

| Lipstick composition | | | | | | |
|---|---|---|---|---|---|---|
| | Example | | | | Comparative Example | |
| | 1 | 2 | 3 | 4 | 1 | 2 |
| (a) Fischer-Tropsch Wax (1) | 9.5 | 9.95 | 8 | — | — | — |
| (a) Fischer-Tropsch Wax (2) | — | — | 1.5 | 9.5 | — | — |
| (b) Microcrystalline wax | 0.5 | 0.05 | 0.5 | 0.5 | — | — |
| Ceresin wax | — | — | — | — | 10 | 10 |
| Carnauba wax | — | — | — | — | 2 | — |
| Candellila wax | — | — | — | — | 3 | — |

TABLE 2-continued

Lipstick composition

|  | Example | | | | Comparative Example | |
|---|---|---|---|---|---|---|
|  | 1 | 2 | 3 | 4 | 1 | 2 |
| Dimethyl polysiloxane | 10 | 10 | 10 | 10 | 10 | 10 |
| Glyceryl isostearate/hydrogenated rosinate | 20 | 20 | 20 | 20 | 20 | 20 |
| Liquid lanolin | 10 | 10 | 10 | 10 | 10 | 10 |
| Glyceryl tri-2-ethylhexanoate | 20 | 20 | 20 | 20 | 15 | 20 |
| Glyceryl diisostearate | 15 | 15 | 15 | 15 | 15 | 15 |
| Diisostearyl malate | 10 | 10 | 10 | 10 | 10 | 10 |
| D&C red No. 7 calcium lake (Red 202) | 2 | 2 | 2 | 2 | 2 | 2 |
| Titanium oxide | 0.5 | 0.5 | 0.5 | 0.5 | 0.5 | 0.5 |
| Iron oxide red | 2 | 2 | 2 | 2 | 2 | 2 |
| Iron oxide black | 0.5 | 0.5 | 0.5 | 0.5 | 0.5 | 0.5 |
| Antioxidant | appropriate amount | | | | | |
| Perfume | appropriate amount | | | | | |
| Shape-retaining ability | ⊚ | ○ | ⊚ | ⊚ | ○ | △ |
| Spreadability | ⊚ | ⊚ | ⊚ | ⊚ | △ | ○ |
| Gloss | ⊚ | ⊚ | ⊚ | ⊚ | ○ | x |

TABLE 3

Lipstick composition

|  | Example | | | |
|---|---|---|---|---|
|  | 5 | 6 | 7 | 8 |
| (a) Fischer-Tropsch Wax (1) | 10 | 10 | 5 | 9.5 |
| (b) Microcrystalline wax | 1 | 2 | 0.5 | 0.5 |
| Candellila wax | 0.5 | — | 2 | — |
| Carnauba wax | 0.5 | — | 2 | — |
| Polyethylene wax | — | — | 5 | 5 |
| Dimethyl polysiloxane | — | 10 | — | 10 |
| Methylphenyl polysiloxine | 20 | — | 10 | 5 |
| Polyoxyethylene/methylpolysiloxane copolymer | — | — | — | 5 |
| Organo polysiloxane | — | — | — | 15 |
| Decamethylcyclopentasiloxane | — | — | — | 30 |
| Diisostearyl malate | 10 | — | 5 | — |
| Glyceryl triisostearate | — | 10 | 20 | — |
| Glyceryl diisostearate | 23 | 5 | 5 | — |
| Glyceryl tri-2-ethylhexanoate | — | 10 | 19.5 | — |
| Glyceryl isostearate/hydrogenated rosinate | 15 | 5 | — | 15 |
| Polybutene | — | 10 | — | — |
| Diglyceryl triisostearate | — | 13 | 10 | — |
| Heptylundecyl Hydroxystearate | — | 10 | — | — |
| Macadamia nut oil | 10 | — | — | — |
| Cholesteryl Macadamiate | 5 | — | — | — |
| Trimethylolpropane trioctanoate | — | 10 | 5 | — |
| Octyl methoxycinnamate | — | — | 5 | — |
| Hydrophobically treated silica | — | — | 1 | — |
| D&C red No. 7 calcium lake | 2 | 2 | 2 | 2 |
| Titanium oxide | 0.5 | 0.5 | 0.5 | 0.5 |
| Iron oxide red | 2 | 2 | 2 | 2 |
| Iron oxide black | 0.5 | 0.5 | 0.5 | 0.5 |
| Antioxidant | appropriate amount | | | |
| Perfume | appropriate amount | | | |
| Shape-retaining ability | ⊚ | ⊚ | ⊚ | ⊚ |
| Spreadability | ⊚ | ⊚ | ○ | ○ |
| Gloss | ⊚ | ⊚ | ○ | ○ |

TABLE 4

Lip gloss

|  | Example 9 |
|---|---|
| (a) Fischer-Tropsch wax (1) | 9 |
| (b) Microcrystalline wax | 1 |
| Glyceryl triisostearate | 20 |
| Glyceryl diisostearate | 4 |
| Glyceryl tri-2-ethylhexanoate | 10 |
| Glyceryl isostearate/hydrogenated rosinate | 30 |
| Liquid lanolin | 5 |
| Cholesteryl Macadamiate | 10 |
| Trimethylolpropane trioctanoate | 10 |
| Pearl pigment | 1 |
| Antioxidant | appropriate amount |
| Perfume | appropriate amount |
| Shape-retaining ability | ⊚ |
| Spreadability | ⊚ |
| Gloss | ⊚ |

TABLE 5

Lip cream (Lip balm)

|  | Example 10 |
|---|---|
| (a) Fischer-Tropsch Wax (1) | 10 |
| (b) Microcrystalline wax | 1 |
| Dimethyl polysiloxane | 10 |
| Glyceryl diisostearate | 15 |
| Glyceryl tri-2-ethylhexanoate | 13.5 |
| Liquid lanolin | 20 |
| Macadamia nuts oil | 15 |
| Jojoba oil | 15 |
| Menthol | 0.5 |
| Antioxidant | appropriate amount |
| Perfume | appropriate amount |
| Shape-retaining ability | ⊚ |
| Spreadability | ⊚ |
| Gloss | ⊚ |

TABLE 6

Foundation

|  | Example 11 | Example 12 |
|---|---|---|
| (a) Fischer-Tropsch Wax (1) | 7 | 9 |
| (b) Microcrystalline wax | 1 | 1 |
| Dimethyl polysiloxane | 10 | 25 |
| Methylphenyl polysiloxane | 5 | 10 |
| Ring type dimethyl silicone oil | 34.9 | — |
| Squalane | 10 | 16.9 |
| Sericite | 12 | 18 |
| Titanium oxide | 15 | 15 |
| Iron oxide red | 1 | 1 |
| Iron oxide yellow | 4 | 4 |
| Iron oxide black | 0.1 | 0.1 |

TABLE 6-continued

Foundation

| | Example 11 | Example 12 |
|---|---|---|
| Antioxidant | appropriate amount | appropriate amount |
| Perfume | appropriate amount | appropriate amount |
| Shape-retaining ability | ⊚ | ⊚ |
| Spreadability | ⊚ | ○ |

TABLE 7

Eye brow pencil

| | Example 13 |
|---|---|
| (a) Fischer-Tropsch Wax (1) | 14 |
| (b) Microcrystalline wax | 2 |
| Dimethyl polysiloxane | 14 |
| Liquid paraffin | 10 |
| Macadamia nuts oil | 10 |
| Glyceryl tri-2-ethylhexanoate | 20 |
| Mica | 10 |
| Iron oxide black | 15 |
| Iron oxide red | 5 |
| Antioxidant | appropriate amount |
| Perfume | appropriate amount |
| Shape-retaining ability | ⊚ |
| Spreadability | ⊚ |

TABLE 8

Hair stick

| | Example 14 |
|---|---|
| (a) Fischer-Tropsch Wax (1) | 10 |
| (b) Microcrystalline wax | 2 |
| Dimethyl polysiloxane | 20 |
| Methylphenyl polysiloxane | 20 |
| Liquid lanolin | 15 |
| Glyceryl tri-2-ethylhexanoate | 23 |
| Liquid paraffin | 10 |
| Antioxidant | appropriate amount |
| Perfume | appropriate amount |
| Shape-retaining ability | ⊚ |
| Spreadability | ⊚ |
| Gloss | ⊚ |

TABLE 9

Lipstick composition

| | Example 15 |
|---|---|
| (a) Fischer-Tropsch Wax (1) | 13 |
| (b) Microcrystalline wax | 1 |
| Dimethyl polysiloxane (6 mPa·s/25° C.) | 5 |
| Decamethyl pentasiloxane | 3 |
| Methyl phenyl polysiloxane | 10 |

TABLE 9-continued

Lipstick composition

| | Example 15 |
|---|---|
| Perfluoroalkyl denatured methylphenyl polysiloxane (= Perfluorooctylethyl/Diphenyl Dimethicone Copolymer) | 24 |
| Alkoxymethylpolysiloxane | 2 |
| Polyoxyethylene/methylpolysiloxane copolymer | 5 |
| Non aqueous polymer dispersion A *1) | 30 |
| D&C red No. 7 calcium lake (Red 202) | 2 |
| Titanium oxide | 0.5 |
| Iron oxide red | 2 |
| Iron oxide black | 0.5 |
| Glycerine | 1 |
| Purified water | 1 |
| Antioxidant | appropriate amount |
| Perfume | appropriate amount |
| Shape-retaining ability | ⊚ |
| Spreadability | ⊚ |
| Gloss | ⊚ |

*1) A Non-aqueous polymer dispersion A was obtained by the process described below:

15 mass % of Methylmetacrylate monomer, 25 mass % of ethylacrylate monomer, 0.1 mass % of polymerization initiator, and 5 mass % of Dimethylpolysiloxane graft polymer (M W=about 150000) as dispersion stabilizer, was added into 54.9 mass % of decamethyl cyclopentasiloxane as dispersion medium. It was mixed at 120° C. for 10 hours in order to polymerize,. Following removal of the monomer under reduced pressure, the reaction mixture was cooled to 25° C. and a milky-white colored non aqueous polymer dispersion was obtained. It was dispersed with polymer particles with an average particle size 1 μm, in a volatile silicone as a dispersion medium.

TABLE 10

Stick shaped emulsion type Lipstick composition

| | Example 16 |
|---|---|
| (a) Fischer-Tropsch Wax (1) | 8 |
| (b) Microcrystalline wax | 2 |
| Heptylundecyl Hydroxystearate | 10 |
| Glyceryl diisostearate | 27 |
| Liquid paraffin | 25 |
| Diglyceryl triisostearate | 20 |
| Dimethyl polysiloxane/polyoxyethylene copolymer | 0.5 |
| Purified water | 1 |
| Glycerine | 0.5 |
| D&C red No. 7 calcium lake (Red 202) | 2 |
| Titanium oxide | 0.5 |
| Iron oxide red | 2 |
| Iron oxide black | 0.5 |
| Cholesteryl Macademiate | 1 |
| Antioxidant | appropriate amount |
| Perfume | appropriate amount |
| Shape-retaining ability | ⊚ |
| Spreadability | ⊚ |
| Gloss | ⊚ |

The present invention provides solid cosmetics, which are superior in terms of shape-retaining ability and usability, and especially superior in Spreadability, gloss and shape-retaining ability simultaneously.

Also, the wax composition of the present invention is superior solidifier for liquid oils.

Also, the present invention provides solid cosmetic without the problem of the production process when the use of high melting point wax.

What is claimed is:

1. A solid cosmetic composition comprising:
   (a) Fischer-Tropsch wax having average molecular weight of 300 to 1200 and
   (b) Microcrystalline wax in the weight ratio of (a):(b)= 60:40 to 99.9: 0.1.

2. The solid cosmetic composition as claimed in claim 1, further comprising a liquid oil component.

3. The solid cosmetic composition as claimed in claim 1, comprising a solidifier consisting of a wax component of (a) and (b).

4. The solid cosmetic composition as claimed in claim 1, which comprises a lipstick composition, which further comprise a colorant and/or a pigment.

5. A wax composition comprising:
   (a) Fischer-Tropsch wax having average molecular weight of 300 to 1200 and
   (b) Microcrystalline wax blended in the weight ratio of (a):(b)=60:40 to 99.9:0.1.

6. A Lipstick composition comprising:
   (a) Fischer-Tropsch wax having average molecular weight of 300 to 1200,
   (b) Microcrystalline wax in the weight ratio of (a):(b)= 60:40 to 99.9:0.1, and
   (c) 30 to 99.9 mass % of a liquid oil component.

7. The lipstick composition as claimed in claim 6, containing 0.1 to 30 mass % of total amount of the ingredient (a) and (b) based on the total amount of the lipstick composition.

8. The lipstick composition as claimed in claim 6, further containing (d) a Colorant and/or a pigment.

* * * * *